(12) United States Patent
Pan (10) Patent No.: US 11,445,865 B2
(45) Date of Patent: Sep. 20, 2022

(54) TOOTHBRUSH STERILIZATION AND DRYING UNIT

(71) Applicant: SHENZHEN CONVL TECH CO., LTD., Guangdong (CN)

(72) Inventor: Liuyun Pan, Guangdong (CN)

(73) Assignee: Shenzhen Convl Tech Co., LTD., Shenzhen (CN)

( * ) Notice: Subject to any disclaimer, the term of this patent is extended or adjusted under 35 U.S.C. 154(b) by 0 days.

(21) Appl. No.: 16/753,332

(22) PCT Filed: Aug. 6, 2019

(86) PCT No.: PCT/CN2019/099434
§ 371 (c)(1),
(2) Date: Apr. 2, 2020

(87) PCT Pub. No.: WO2020/206887
PCT Pub. Date: Oct. 15, 2020

(65) Prior Publication Data
US 2022/0015586 A1 Jan. 20, 2022

(30) Foreign Application Priority Data

Apr. 9, 2019 (CN) .......................... 201920489690.X (51) Int. Cl.
*A47K 5/18* (2006.01)
*A61L 2/10* (2006.01)
(52) U.S. Cl.
CPC . *A47K 5/18* (2013.01); *A61L 2/10* (2013.01)

(58) Field of Classification Search
CPC ..... A47K 5/18; A61L 2/10; A61L 2/26; F26B 21/00
See application file for complete search history.

(56) References Cited

U.S. PATENT DOCUMENTS

2017/0106108 A1\* 4/2017 Lee .................. A46B 17/06

FOREIGN PATENT DOCUMENTS

| CN | 2805646 Y | 8/2006 |
|---|---|---|
| CN | 202235072 U | 5/2012 |
| CN | 203609350 U | 5/2014 |
| CN | 104207701 A | 12/2014 |
| CN | 204016119 U | 12/2014 |
| CN | 204207647 U | 3/2015 |
| CN | 104799651 A | 7/2015 |

(Continued)

*Primary Examiner* — Britt D Hanley
(74) *Attorney, Agent, or Firm* — Robert L. Stearns; Dickinson Wright, PLLC (57) ABSTRACT

The present solution provides a gargling cup, which includes: a cup body; a cup lid assembly configured to be covered on the cup body; a sterilization unit arranged on the cup lid assembly for sterilizing the cup body; a drying unit arranged on the cap lid assembly for drying the cup body. The gargling cup provided by this solution is configured for sterilizing and drying the cup body by the arrangement of the sterilization unit and the drying unit to prevent the cup body from breeding bacteria. The sterilization unit and the drying unit are both arranged on the cap lid assembly, so that the cup body is light and configured for holding enough water, and there is no need to worry that the water in the cup body will affect the service life of the sterilization unit and the drying unit.

8 Claims, 6 Drawing Sheets

(56) References Cited

FOREIGN PATENT DOCUMENTS

| | | |
|---|---|---|
| CN | 204971020 U | 1/2016 |
| CN | 105615504 A | 6/2016 |
| CN | 208319588 U | 1/2019 |
| KR | 100557780 B1 * | 3/2006 |
| KR | 20140001626 U | 3/2014 |

* cited by examiner

TOOTHBRUSH STERILIZATION AND DRYING UNIT

CROSS REFERENCE TO RELATED APPLICATIONS

The present application is a 35 U.S.C. § 371 national stage application of PCT Application Ser. No. PCT/CN2019/099434, filed on Aug. 6, 2019, which claims priority to Chinese Patent Application Ser. No. CN201920489690.X, filed on Apr. 9, 2019, the entire contents of which are incorporated herein by reference in their entireties.

TECHNICAL FIELD

The present application relates to the technical field of daily necessities, and more particularly to a gargling cup.

BACKGROUND

The gargling cups used in daily life usually do not have a lid, thus dust particles, bacteria and pathogenic microorganisms floating in the air will enter the cup. The dust particles will fall on the toothbrush and then enter our digestive system through the mouth, thereby causing diarrhea. Bacteria and pathogenic microorganisms are more harmful. After entering the cup, they will multiply on the cup wall and toothbrush. When the amount reaches a certain level, we will be sick. Even with the lid, it can only block the dust particles. Because the cup is not ventilated, the toothbrush is in a humid environment for a long time, which accelerates the proliferation of bacteria and pathogenic microorganisms on the cup wall and toothbrush, thereby bringing us more harm. In addition, some viruses can survive for a long time in normal temperature and humid environment, which will also bring serious harm to our health.

Technical Problem

The objective of the present application is to provide a gargling cup to solve the technical problem that the gargling cup in the prior art is prone to breed bacteria under a humid and unventilated environment for a long time.

Technical Solutions

In order to achieve the above-said objective, the present application provides a gargling cup, including:
a cup body;
a cup lid assembly, configured to be covered on the cup body;
a sterilization unit, configured to be arranged on the cup lid assembly for sterilizing the cup body; and
a drying unit, configured to be arranged on the cup lid assembly for drying the cup body.

Further, the cup lid assembly includes:
a lower lid, configured to be covered on the cup body; and
an upper lid, configured to be fixedly connected to the lower lid;
wherein the upper lid and the lower lid are enclosed to form an installation cavity, and the sterilization unit and the drying unit are both disposed in the installation cavity.

Further, the sterilization unit includes:
a circuit board, disposed in the installation cavity; and
a plurality of UV lamps, disposed on the circuit board and are electrically connected to the circuit board;
wherein the lower lid defines a plurality of through holes, and the UV lamps passes through the through holes to sterilize the cup body.

Further, the drying unit includes a fan, and the fan is disposed in the installation cavity and is electrically connected to the circuit board.

Further, a fan chamber is provided in the installation cavity, and the fan is disposed in the fan chamber; the fan chamber extends from the upper lid to the lower lid, the upper lid defines a plurality of air inlets communicating with the fan chamber, the lower lid defines a plurality of vents connecting the fan chamber and the cup body, and a junction of the cup body and the lower lid are provided with a plurality of air outlets.

Further, the upper lid is provided with a first cylinder extending towards the lower lid, the lower lid is provided with a second cylinder extending towards the upper lid, and an end of the first cylinder and an end of the second cylinder are concavely and convexly enclosed to form the fan chamber.

Further, the upper lid defines a plurality of the air inlets, the air inlets are correspondingly disposed above the fan chamber and are evenly distributed along a radial direction of the upper lid, and an arc length of each of the air inlets gradually increases from the center to the periphery along the radial direction of the upper lid.

Further, a top portion of the cup body has a first joining surface, the lower lid has a second joining surface, the first joining surface and/or the second joining surface is wavy, and the first joining surface and the second joining surface are enclosed to form a plurality of the air outlets.

Further, the circuit board is provided with two first pins, the upper lid defines first inserting holes, and external power supply cords are electrically connected to the two first pins in the first inserting holes to charge the circuit board.

Further, the upper lid is provided with a wire slot thereon for receiving the external power supply cords.

Beneficial Effects

The gargling cup provided by the present application has the beneficial effect that compared with the prior art, the gargling cup of the present application is provided with a sterilization unit and a drying unit, so that the cup body can be configured to be sterilized and dried at the same time when the cup body is not used, so as to prevent bacteria from breeding. In addition, the present application separates the cup body from the cup lid assembly, and sets the sterilization unit and the drying unit on the cup lid assembly, so that when brushing teeth with the cup body, the cup body is light and can hold enough water, and it is not needed to worry that the water in the cup will affect the service life of the sterilization unit and drying unit.

BRIEF DESCRIPTION OF THE DRAWINGS

In order to explain the technical solutions in the embodiments of the present application more clearly, the drawings used in the embodiments or the description of the prior art will be briefly introduced below. Obviously, the drawings in the following description are only some embodiments of the present application, and for those of ordinary skill in the art, other drawings may be obtained based on these drawings without paying creative labor.

Reference numerals in the drawings are as follows:
1—cup body; 2—cup lid assembly; 3—sterilization unit; 4—drying unit; 10—air outlet; 11—first joining surface; 20—installation cavity; 21—upper lid; 22—lower lid; 23—decorative sheet; 24—fan chamber; 31—circuit board; 32—UV lamp; 41—fan; 211—first screw post; 212—first inserting hole; 213—wire slot; 214—air inlet; 215—first cylinder; 220—through hole; 221—second screw post; 222—positioning post; 223—second inserting hole; 224—vent; 225—second cylinder; 226—annular convex portion; 311—first pin; 312—second pin; 2131—engagement plate; 2250—wire hole; 2261—second joining surface; 2262—annular groove.

EMBODIMENTS OF THE INVENTION

In order to make the technical problems, technical solutions and beneficial effects of the present application to be more clearly understood, the present application will be further described in detail with reference to the accompanying drawings and embodiments. It should be understood that the specific embodiments described herein are only used to explain the present application and are not intended to limit the present application.

It should be noted that when an element is referred to as being "fixed to" or "disposed on" another element, it may be directly or indirectly fixed to/disposed on the other element. When an element is referred to as being "connected to" another element, it can be configured to be directly or indirectly connected to the other element.

It should be understood that the terms "length", "width", "upper", "lower", "front", "rear", "left", "right", "vertical", "horizontal", "top", "bottom", "inner", "outer", etc. indicate orientations or positional relationships based on the orientations or positional relationships shown in the drawings, only for convenience of describing the present application and simplifying the description, rather than indicating or implying that the device or element referred to must have a particular orientation, or be constructed and operated in a particular orientation, therefore they should not be construed as limiting the present application.

In addition, the terms "first" and "second" are used for descriptive purposes only and cannot be understood as indicating or implying relative importance or implicitly indicating the number of technical features indicated. Therefore, the features defined as "first" and "second" may explicitly or implicitly include one or more of the features. In the description of the present application, the meaning of "a plurality of" is two or more, unless it is specifically defined otherwise.

Figure 1:
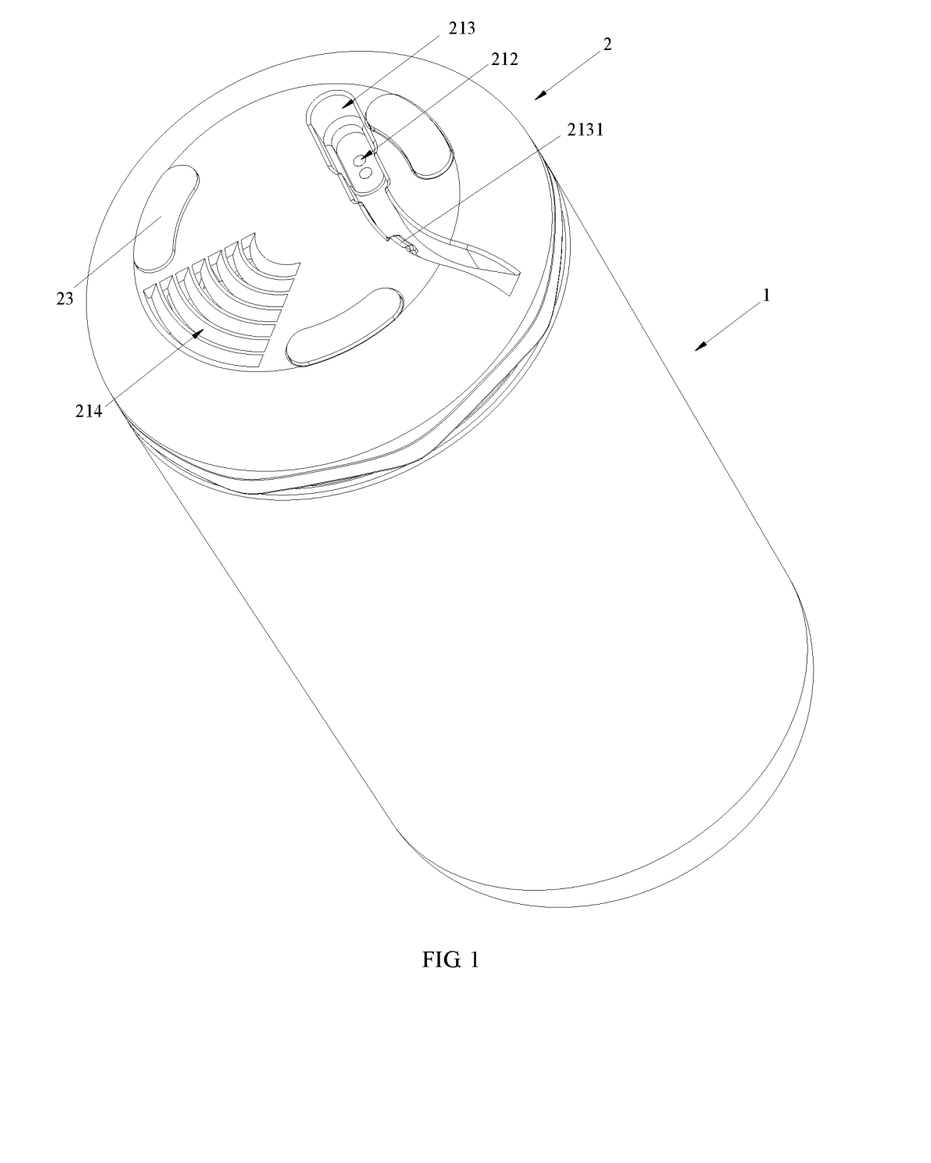
FIG. 1 is a schematic perspective view of a gargling cup provided by an embodiment of the present application.
Figure 2:
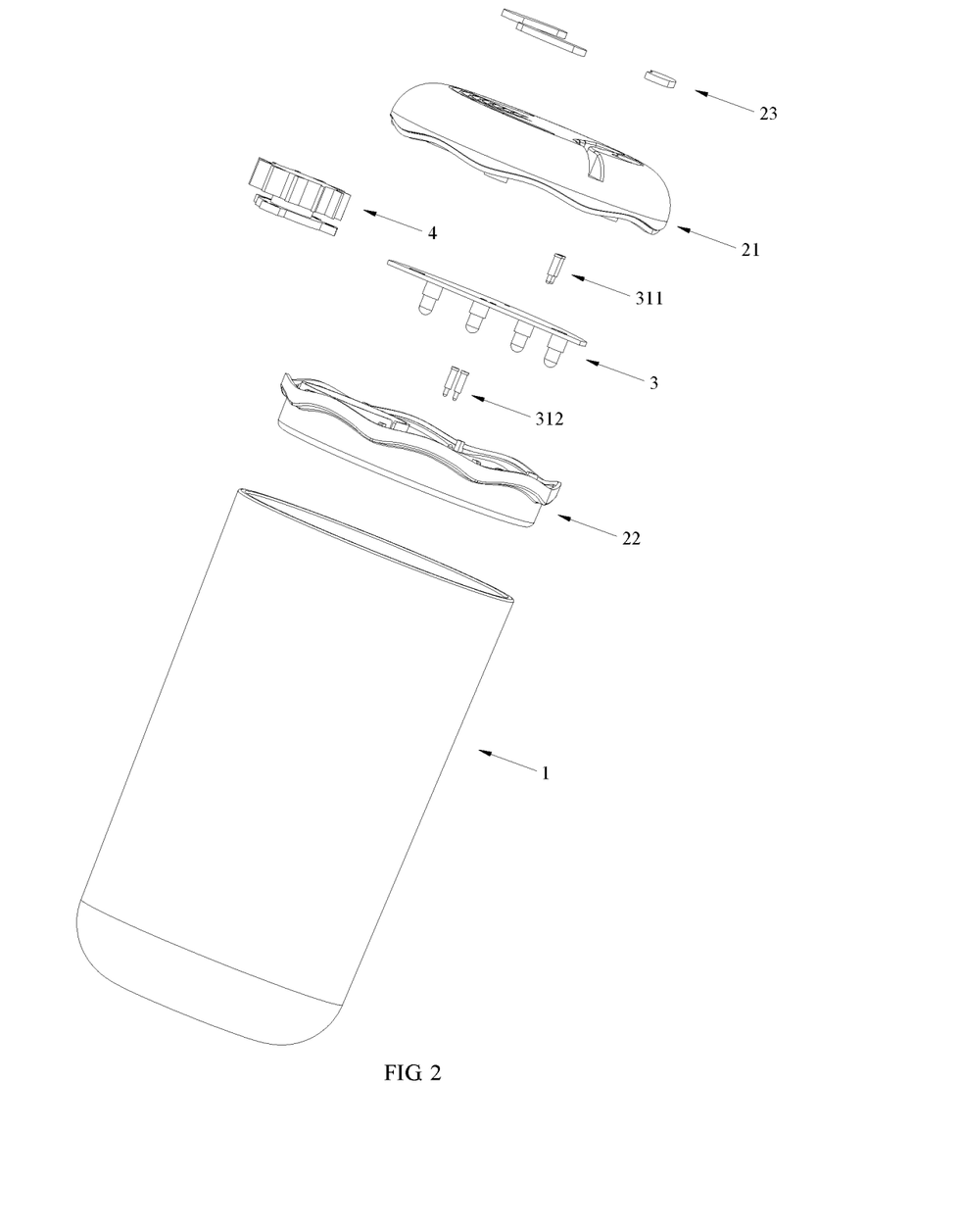
FIG. 2 is an exploded view of the gargling cup in FIG. 1.
Figure 3:
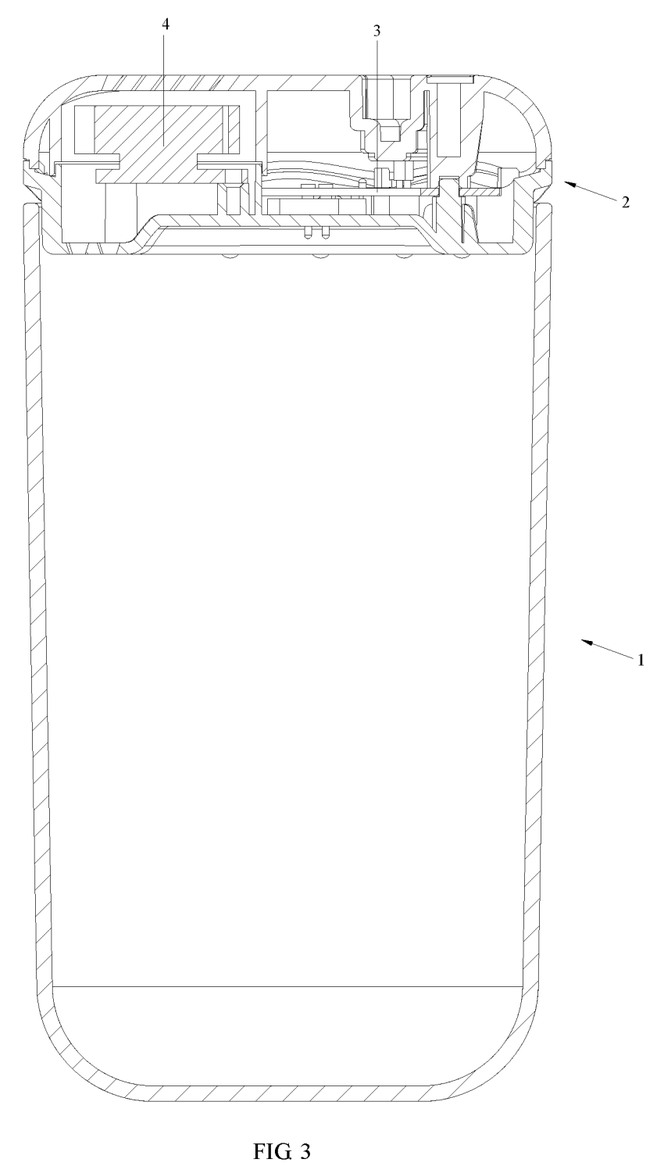
FIG. 3 is a schematic cross-sectional view of the gargling cup in FIG. 1.

Referring to FIGS. 1-3, the gargling cup provided by the present application will be described.

The gargling cup includes a cup body 1, a cup lid assembly 2, a sterilization unit 3, and a drying unit 4.

The cup body 1 is any container that can be used to hold water for people to brush their teeth. The cup body 1 can be configured to be a plastic cup or a metal cup according to actual needs, and the outer wall of the cup body 1 can be configured to be provided with or without a handle.

The cup lid assembly 2 can be configured to be covered on the cup body 1, that is, when brushing teeth, the cup lid assembly 2 can be removed from the cup body 1, while when not brushing teeth, the cup lid assembly 2 can be configured to be covered on the cup body 1. Thus, dust particles, bacteria and pathogenic microorganisms in the air are prevented from entering the cup body 1.

The sterilization unit 3 is arranged on the cup lid assembly 2. The sterilization unit 3 is used to sterilize the cup body 1, that is, when not brushing teeth, the cup lid assembly 2 can be configured to be covered on the cup body 1, and the sterilization unit 3 is used to sterilize the cup body 1.

The drying unit 4 is arranged on the cup lid assembly 2. The drying unit 4 is used to dry the cup body 1. After the teeth are brushed, the drying unit 3 is used to dry the cup body 1 in time to prevent bacteria and pathogenic microorganisms from multiplying in humid environment.

The gargling cup provided by the present application is provided with the sterilization unit 3 and the drying unit 4, so that when the cup body 1 is not used, the cup body 1 can be configured to be sterilized and disinfected, and at the same time the cup body 1 is dried to prevent bacteria from breeding and multiplying. In addition, the present application separates the cup body 1 from the cup lid assembly 2 and sets the sterilization unit 3 and the drying unit 4 on the cup lid assembly 2, so that when the cup body 1 is used for brushing teeth, the cup body 1 is light and can hold enough water, and there is no need to worry that the water in the cup body 1 will affect the service life of the sterilization unit 3 and the drying unit 4.

Figure 4:
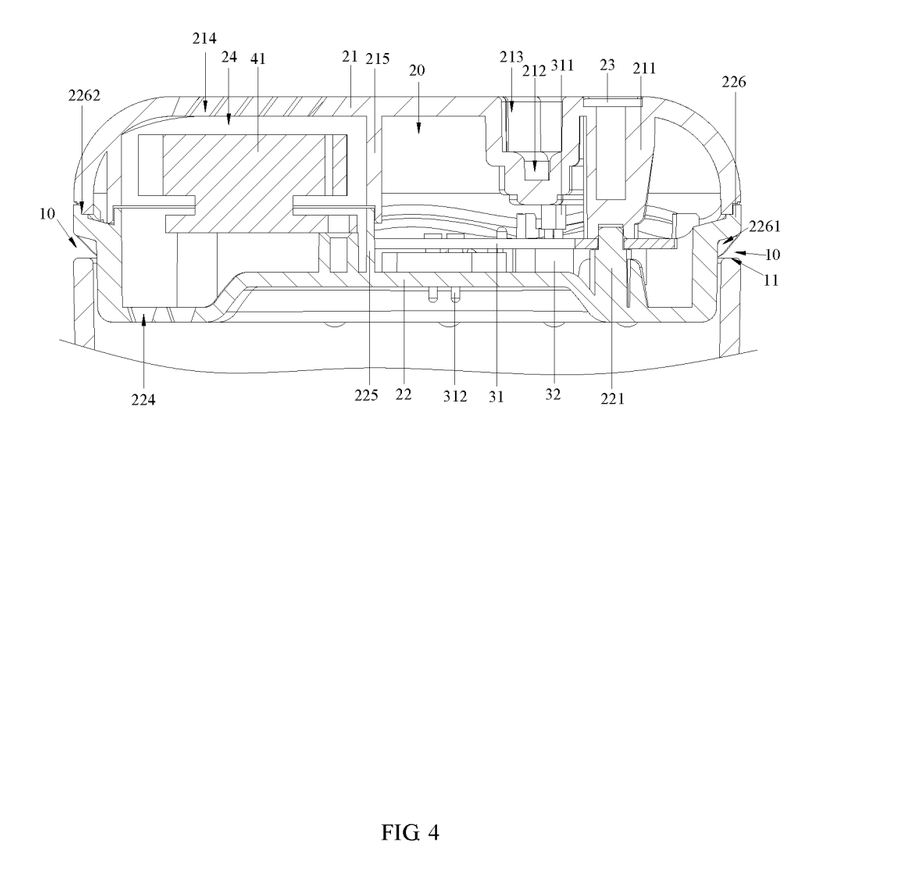
FIG. 4 is a partially enlarged view of the gargling cup in FIG. 3.

Further, referring to FIG. 2 and FIG. 4, as a specific embodiment of the gargling cup provided by the present application, the cup lid assembly 2 includes an upper lid 21 and a lower lid 22. The lower lid 22 can be configured to be covered on the cup body 1. The upper lid 21 and the lower lid 22 are fixedly connected, and the upper lid 21 and the lower lid 22 are enclosed to form an installation cavity 20. The sterilization unit 3 and the drying unit 4 are both disposed in the installation cavity 20. Specifically, in this embodiment, the lower lid 22 and the upper lid 21 are both U-shaped, the opening of the lower lid 22 is disposed opposite to the opening of the upper lid 21, and the upper lid 21 and the lower lid 22 are enclosed to form a cylindrical installation cavity 20.

In this embodiment, the end of the upper lid 21 and the end of the lower lid 22 are concavely and convexly matched to form a sealed connection. The upper lid 21 is provided with first screw posts 211 penetrating the upper lid 21, the lower lid 22 is provided with second screw posts 221, and the upper lid 21 and the lower lid 22 are locked by screws. Specifically, during the installation, the sterilization unit 3 and the drying unit 4 can be configured to be installed on the lower lid 22 first, then the upper lid 21 is covered, and finally the upper lid 21 and the lower lid 22 is locked by the screws downward from the top of the upper lid 21.

Preferably, in this embodiment, referring to FIG. 1, decorative sheets 23 are provided on the upper lid 21, and the decorative sheets 23 are covered on the first screw posts 211 respectively. The decorative sheets 23 can prevent screw heads from being exposed to the outside of the gargling cup, thus affecting the beauty of the cup. Specifically, the material of the decoration sheets 23 is soft rubber, and the color of the decoration sheets 23 can be selected to match with the upper lid 21, or can be matched according to requirements.

Preferably, in this embodiment, referring to FIG. 1, the upper lid 21 is provided with three decorative sheets 23, each of which is waist-shaped, and the three decorative sheets 23 are evenly distributed along the circumference of the upper lid 21, so that the appearance of the gargling cup is beautiful.

Figure 5:
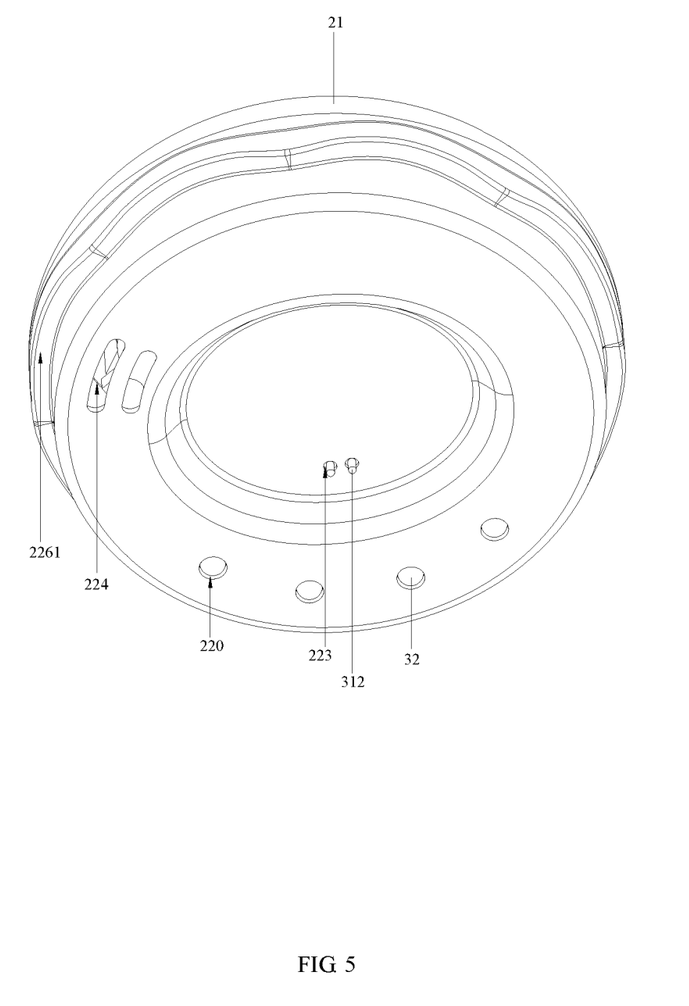
FIG. 5 is a schematic bottom view of the gargling cup in FIG. 1 after removing the cup body.

Further, referring to FIG. 4, as a specific embodiment of the gargling cup provided by the present application, the sterilization unit 3 includes a circuit board 31 and UV lamps 32. The circuit board 31 is disposed in the installation cavity 20, and the UV lamps 32 are provided on the circuit board 31 and electrically connected to the circuit board 31. As shown in FIG. 5, the lower lid 22 defines a plurality of through holes 220, and UV lamps 32 passes through the corresponding through holes 220 to sterilize the cup body 1. Specifically, in this embodiment, the diameters of the through holes 220 are matched with the diameters of the UV lamps 32. The lamp base of the UV lamp 32 is disposed in the through hole 220 and partially penetrates the through hole 220, and the UV light emitted by the UV lamps 32 illuminates the cup body 1 to sterilize the cup body 1.

In this embodiment, the sterilization unit 3 sterilizes the cup body 1 with UV lamps 32. It can be understood that, in other embodiments of the present application, the sterilization unit 3 can also sterilize the cup body 1 through far-infrared ray, which is not limited here.

In this embodiment, referring to FIG. 5, four UV lamp lamps 32 are arranged on the circuit board 31. Correspondingly, the lower lid 22 defines four through holes 220 distributed along the circumference of the lower lid 22. The UV lamps 32 are centrally disposed on one side of the cup lid assembly 2, and the drying unit 4 is disposed on the other side of the cup lid assembly 2. It can be understood that, in other embodiments of the present application, two, three, five, and more than five UV lamp lamps 32 may be provided on the circuit board 31, which is not limited here.

Figure 6:
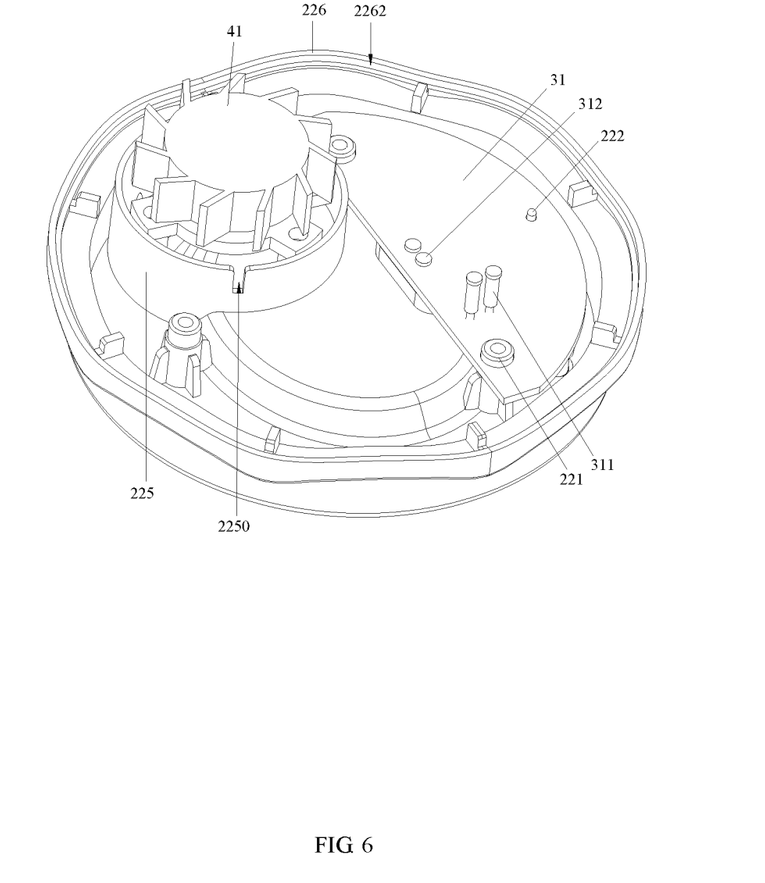
FIG. 6 is a schematic view showing the installation of the sterilization unit and the drying unit on the lower lid in FIG. 1.

Preferably, in this embodiment, referring to FIG. 6, the circuit board 31 is a small semi-circle, a positioning post 222 is disposed on the lower lid 22, and the circuit board 31 is positioned by the positioning post 222. The circuit board 31 is provided with two fixing holes (not shown in the figure), and screws for fixing the connection between the upper lid 21 and the lower lid 22 pass through the fixing holes, thereby locking the circuit board 31 between the upper lid 21 and the lower lid 22.

Further, referring to FIG. 4 and FIG. 6, as a specific embodiment of the gargling cup provided by the present application, the circuit board 31 is provided with two first pins 311, and the two first pins 311 are inserted on the circuit board 31 and electrically connected to the circuit board 31. The upper lid 21 is provided with two first inserting holes 212. The two first pins 311 are exposed outside the upper lid 21 through the two first inserting holes 212. The external power supply cord is electrically connected to the two first pins 311 in the first inserting holes 212 to charge the circuit board 31. In should be understood that, in other embodiments of the present application, the circuit board 31 may also be electrically connected to an external power source through other sockets, which is not limited here.

Preferably, in this embodiment, referring to FIG. 1, the top cover 21 is further provided with a wire slot 213 on the top thereof, the wire slot 213 communicates with the first inserting holes 212, and the wire slot 213 is used to receive an external power supply cord, thereby facilitating the charging of the circuit board 31. In addition, the side wall of the wire slot 213 is provided with an engagement plate 2131 for limiting the external power supply cord, thereby preventing the external power supply cord from falling off during the charging process.

Further, in this embodiment, the circuit board 31 is further provided with two second pins 312. The two second pins 312 are inserted on the circuit board 31 and electrically connected to the circuit board 31. The bottom of the lower lid 22 defines two second inserting holes 223, and the two second pins 312 respectively pass through the two second inserting holes 223 and are exposed to the outside of the lower lid 22. The two second pins 312 can be configured to be electrically connected to the electric toothbrush so as to sterilize, disinfect and dry the electric toothbrush. During use, the cup body 1 can be removed, and then the two second pins 312 can be configured to be electrically connected to the electric toothbrush, so that the electric toothbrush can be configured to be sterilized and dried.

Further, referring to FIG. 4 and FIG. 6, as a specific embodiment of the gargling cup provided by the present application, the upper drying unit 4 includes a fan 41 which is disposed in the installation cavity 20 and electrically connected to the circuit board 31. The fan 41 is used to blow the cup body 1 so as to dry the cup body 1. It should be understood that, in other embodiments of the present application, the cup body 1 may be dried by a heat pipe or the like, which is not limited here.

Further, referring to FIG. 4, as a specific embodiment of the gargling cup provided by the present application, a fan chamber 24 is disposed in the installation cavity 20, and the fan 41 is disposed in the fan chamber 24. Specifically, the fan chamber 24 extends from the upper lid 21 to the lower lid 22, that is, the upper end of the fan chamber 24 is connected to the upper lid 21, and the lower end of the fan chamber 24 is connected to the lower lid 22. The upper lid 21 defines air inlets 214 communicating with the fan chamber 24, the lower lid 22 defines vents 224 connecting the fan chamber 24 and the cup body 1, and the junction of the cup body 1 and the lower lid 22 is provided with air outlets 10, so that the air inlets 214, the fan chamber 24, the fan 41, the vents 224, the cup body 1 and the air outlets 10 are formed to form a drying system. The wind in the air enters the fan chamber 24 from the air inlets 214 under the suction power of the fan 41, and enters the cup body 1 from the vents 224 under the driving force of the fan 41 so as to dry the cup body 1, and the wet and cold air flows out from the air outlets 10 to the air, forming an air circulation flow.

In this embodiment, the fan chamber 24 is provided, so that the air absorption force of the fan 41 is stronger, and the drying effect of the fan 41 on the cup body 1 is better. It should be understood that, in other embodiments of the present application, the fan chamber 24 may not be provided in the installation cavity 20, and the fan 41 is directly disposed in the installation cavity 20, which is not limited here.

Further, referring to FIG. 4, as a specific embodiment of the gargling cup provided by the present application, the upper lid 21 is provide with a first cylinder 215 extending towards the direction of the lower lid 22, and the lower lid 22 is provided with a second cylinder 225 extending towards the direction of the upper lid 21. The end of the first cylinder 215 and the end of the second cylinder 225 are concavely and convexly enclosed to form a fan chamber 24, so that the fan chamber 24 is sealed and isolated from the installation cavity 20, thereby further improving the drying effect of the fan 41. Specifically, the first cylinder 215 and the upper lid 21 are integrally formed, and the second cylinder 225 and the lower lid 22 are integrally formed. Referring to FIG. 6, the circuit board 31 is disposed beside the fan chamber 24. The second cylinder 225 defines a wire hole 2250, and the connecting wire connecting the fan 41 and the circuit board 31 passes through the wire hole 2250.

Further, referring to FIG. 1, as a specific embodiment of the gargling cup provided by the present application, the upper lid 21 defines a plurality of air inlets 214, and each air inlet 214 is correspondingly disposed above the fan chamber 24. The air inlets 214 form a fan-shaped structure. Specifically, the air inlets 214 are evenly distributed along the radial direction of the upper lid 21, and each air inlet 214 is arc-shaped. The arc length of each air inlet 214 gradually increases from the center to the periphery along the radial direction of the upper lid 21, and each air inlet 214 is obliquely disposed along the radial direction of the upper lid 21, so that not only the wind in the air can be quickly entered into the fan chamber 24 by the fan 41, but also the appearance of the upper lid 21 is beautiful. It can be understood that, in other embodiments of the present application, according to the specific position of the fan 41 and the actual rotation direction of the fan 41, the air inlets 214 may also be provided in other shapes and other positions, which is not limited here.

Preferably, in this embodiment, the lower lid 22 is provided with two vents 224. The two vents 224 are also arc-shaped and distributed along the radial direction of the lower lid 22, and the two vents 224 are disposed near the edge of the lower lid 22.

Further, referring to FIG. 4, as a specific embodiment of the gargling cup provided by the present application, the top portion of the cup body 1 has a first joining surface 11, and the lower lid 22 has a second joining surface 2261. The joining surface 11 is a flat surface, and the second joining surface 2261 is wavy along the axial direction of the gargling cup. The first joining surface 11 and the second joining surface 2261 are enclosed to from a plurality of air outlets 10, each air outlet 10 communicates with the cup body 1 and the air outlets 10 are evenly distributed along the circumferential direction of the cup body 1. In this embodiment, each air outlet 10 is formed by an enclosure of a wavy surface and a plane, so that not only the lower lid 22 can be configured to be covered on the cup body 1, but also air outlets 10 for air flowing out of the cup body 1 can be configured to be formed between the lower lid 22 and the cup body 1. Of course, in other embodiments of the present application, according to actual conditions and specific requirements, the second joining surface 2261 may not be wavy, which can be realized as long as there is a plurality of gaps formed between the second joining surface 2261 and the first joining surface 11, which is not limited here.

In other embodiments of the present application, the second joining surface 2261 is a flat surface, the first joining surface 11 is wavy along the axial direction of the gargling cup, and the first joining surface 11 and the second joining surface 2261 are enclosed to form a plurality of air outlets 10.

In some other embodiments of the present application, the first joining surface 11 and the second joining surface 2261 are wavy along the axial direction of the gargling cup, the first joining surface 11 is disposed opposite to the second joining surface 2261, and the first joining surface 11 and the second joining surface 2261 are enclosed to form a plurality of air outlets 10.

Specifically, in this embodiment, the outer side wall of the top end of the lower lid 22 extends outwards with an annular convex portion 226, the annular convex portion 226 may be disposed at the top end of the cup body 1, and the bottom surface of the annular convex portion 226 is the second joining surface 2261.

In addition, in order to adapt to the above-mentioned second joining surface 2261, the annular convex portion 226 is provided in a wave shape along the axial direction of the gargling cup. The top portion of the annular convex portion 226 defines an annular groove 2262, and the bottom end of the upper lid 21 is inserted in the annular groove 2262 to form a connection. In order to ensure that the upper lid 21 and the lower lid 22 are tightly connected, the bottom end of the upper lid 21 is also provided in a wave shape.

The above are only the preferred embodiments of the present application and are not intended to limit the present application. Any modification, equivalent replacement, and improvement made within the spirit and principle of the present application shall be included in the protection scope of the present application.

What is claimed is:

1. A gargling cup, comprising:
   a cup body;
   a cup lid assembly, configured to be covered on the cup body;
   a sterilization unit, configured to be arranged on the cup lid assembly for sterilizing the cup body; and
   a drying unit, configured to be arranged on the cup lid assembly for drying the cup body;
   wherein the drying unit comprises a fan, and the fan is disposed in the installation cavity and is electrically connected to the circuit board, a fan chamber is provided in the installation cavity, and the fan is disposed in the fan chamber; the fan chamber extends from an upper lid to a lower lid, the upper lid defines a plurality of air inlets communicating with the fan chamber, the lower lid defines a plurality of vents connecting the fan chamber and the cup body, and a junction of the cup body and the lower lid are provided with a plurality of air outlets.

2. The gargling cup according to claim 1, wherein the cup lid assembly comprises:
   a lower lid, configured to be covered on the cup body; and
   an upper lid, configured to be fixedly connected to the lower lid;
   wherein the upper lid and the lower lid are enclosed to form an installation cavity, and the sterilization unit and the drying unit are both disposed in the installation cavity.

3. The gargling cup according to claim 2, wherein the sterilization unit comprises:
   a circuit board, disposed in the installation cavity; and
   a plurality of UV lamps, disposed on the circuit board and are electrically connected to the circuit board;
   wherein the lower lid defines a plurality of through holes, and the UV lamps passes through the through holes to sterilize the cup body.

4. The gargling cup according to claim 1, wherein the upper lid is provided with a first cylinder extending towards the lower lid, the lower lid is provided with a second cylinder extending towards the upper lid, and an end of the first cylinder and an end of the second cylinder are concavely and convexly enclosed to form the fan chamber.

5. The gargling cup according to claim 1, wherein the upper lid defines a plurality of the air inlets, the air inlets are correspondingly disposed above the fan chamber and are evenly distributed along a radial direction of the upper lid, and an arc length of each of the air inlets gradually increases from the center to the periphery along the radial direction of the upper lid.

6. The gargling cup according to claim 1, wherein a top portion of the cup body has a first joining surface, the lower lid has a second joining surface, the first joining surface and/or the second joining surface is wavy, and the first joining surface and the second joining surface are enclosed to form a plurality of the air outlets.

7. The gargling cup according to claim 3, wherein the circuit board is provided with two first pins, the upper lid defines first inserting holes, and external power supply cords are electrically connected to the two first pins in the first inserting holes to charge the circuit board.

8. The gargling cup according to claim 7, wherein the upper lid is provided with a wire slot thereon for receiving the external power supply cords.

\* \* \* \* \*